(12) United States Patent
Kumagai et al.

(10) Patent No.: US 6,911,425 B2
(45) Date of Patent: Jun. 28, 2005

(54) INTEGRIN BINDING MOTIF CONTAINING PEPTIDES AND METHODS OF TREATING SKELETAL DISEASES

(75) Inventors: Yoshinari Kumagai, Austin, TX (US); Toshiyuki Yoneda, San Antonio, TX (US); Russell Wayne Blacher, Castro Valley, CA (US)

(73) Assignee: Acologix, Inc., Emeryville, CA (US)

( * ) Notice: Subject to any disclaimer, the term of this patent is extended or adjusted under 35 U.S.C. 154(b) by 138 days.

(21) Appl. No.: 09/812,485

(22) Filed: Mar. 19, 2001

(65) Prior Publication Data

US 2002/0197267 A1 Dec. 26, 2002

Related U.S. Application Data

(63) Continuation-in-part of application No. 09/641,034, filed on Aug. 16, 2000.
(51) Int. Cl.⁷ .................... A61K 38/00; C07K 11/00; C07K 14/00
(52) U.S. Cl. .................. 514/2; 514/12; 514/14; 514/15; 530/300; 530/324; 530/325; 530/326; 530/327; 530/334; 530/344; 435/69.1
(58) Field of Search ............... 514/2, 12, 14, 514/15; 530/300, 324, 325, 326, 327, 334, 344; 435/69.1

(56) References Cited

U.S. PATENT DOCUMENTS

5,849,865 A * 12/1998 Cheng et al. ............... 530/317
6,146,655 A    11/2000 Ruben
6,673,900 B2 *  1/2004 Rowe ......................... 530/350

FOREIGN PATENT DOCUMENTS

| WO | WO 95/14714 A  | 6/1995  |
|----|---------------|---------|
| WO | WO 99/08730 A  | 2/1999  |
| WO | WO 99/48909    | 2/1999  |
| WO | WO 99/48909 A2 | 9/1999  |
| WO | WO 99/60017 A2 | 11/1999 |
| WO | WO 02/05836 A  | 1/2002  |

OTHER PUBLICATIONS

Chappard et al., (1995) "Effects of tiludronate on bone loss in paraplegic patients." *Journal of Bone and Mineral Research*, 10(1):112–118.
Fratzl et al., (1994) "Abnormal bone mineralization after fluoride treatment in osteoporosis: a small–angle x–ray–scattering study." *Journal of Bone and Mineral Research*, 9(10):1541–1549.
Gennari et al., (1994) "Management of osteoporosis and Paget's disease. An appraisal of the risks and benefits of drug treatment." *Drug Saf.*, 11(3):179–95.
Gronowicz et al., (1994) "Synthetic peptide containing Arg–Gly–Asp inhibits bone formation and resorption in a mineralizing organ culture system of fetal rat parietal bones." *Journal of Bone and Mineral Research*, 9(2):193–201.
Hilfiker, (1998) "Characterization of a murine type II sodium–phosphate cotransporter expressed in mammalian small intestine." *Proc. Natl. Acad. Sci. USA*, 95(24):14564–14569.
Lufkin et al., (1994) "Pamidronate: an unrecognized problem in gastrointestinal tolerability." *Osteoporos. Int.*, 4(6):320–322.
Mundy et al., (1999) "Stimulation of bone formation in vitro and in rodents by statins." *Science*, 286:1946–1949.
Rowe et al., (2000) "MEPE, a new gene expressed in bone marrow and tumors causing osteomalacia." *Genomics*, 67:54–68.
Schneider et al., (1995) "Does HRT modify risk of gynecological cancers?" *Int. J. Fertil. Menopausal Study*, 40(1):40–53.
Traianedes et al., (1998) "5–Lipoxygenase metabolites inhibit bone formation in vitro." *Endocrinology*, 139:3178–3184.
Bairoch et al. (1990) "EF–hand motifs in inositol phospholipid–specific phospholipase C. " *FEBS*, vol. 269(2):454–456.
Chauvaux et al. (1990) "Calcium–binding affinity and calcium–enhanced activity of Clostridium thermocellum endoglucanase D. " *Biochem. J.*, vol. 265:261–265.
Davis (1990) "The many Faces of Epidermal Growth Factor Repeats. " *The New Biologist*, vol. 2(5):410–419.
Economou et al. (1990) "The Rhizobium nodulation gene nodO encodes a $Ca^{2+}$–binding protein that is exported without N–terminal cleavage and is homologous to haemolysin and related proteins." *The EMBO Journal*, vol. 9(2):349–354.
Kawasaki et al. (1995) "Calcium–Binding Proteins 1: EF–hands. " *Protein Profile*, vol. 2(4):305–356.
Moncrief et al. (1990) "Evolution of EF–Hand Calcium–Modulated Proteins. I. Relationships Based on Amino Acid Sequences. " *J. Mol. Evol.*, vol. 30:522–562.
Schafer et al. (1995) "Isolation of a YAC Clone Covering a Cluster of Nine S100 Genes on Human Chromosome 1q21: Rationale for a New Nomenclature of the S100 Calcium–Binding Protein Family. " *Genomics*, vol. 25:638–643.

(Continued)

Primary Examiner—Jon Weber
Assistant Examiner—Chih-Min Kam
(74) Attorney, Agent, or Firm—Karl Bozicevic; Bozicevic, Field & Francis LLP

(57) ABSTRACT

Peptide sequences comprising 10 to 50 amino acids are disclosed. The sequences are characterized by containing at least one of an integrin binding motif such as an RGD sequence, a glycosaminoglycan binding motif, and a calcium binding motif, and the remainder of amino acids contiguous with the RGD sequence in matrix extracellular phosphoglycoprotein. The sequences may be formulated for injection or dispersed in toothpaste or a mouthwash or gum patch and administered to enhance bone/tooth growth and/or reduce excessive urinary phosphate loss from the body.

4 Claims, 6 Drawing Sheets

OTHER PUBLICATIONS

Springer et al. (2000) "A Novel $Ca^{2+}$ Binding β Hairpin Loop Better Resembles Integrin Sequence Motifs than the EF Hand." *Cell*, vol. 102:275–377.

Ferris D. M. et al., "RGD–coated titanium implants stimulate increased bone formation in vivo" Biomaterials, Vo. 20, No. 23–24, Dec. 1999. pp. 2323–2331.

Hayashibara T. et al., "A synthetic peptide fragment of human MEPE stimulates new bone formation in vitro and in vivo" Journal of Bone and Mineral Research, New York, NY., US, vol. 19, No. 3, Mar. 2004, pp. 455–462.

Lopez–Moratalla et al., "A common structural motif in Immunopotentiating peptides with sequences present in human autoantigens. Elicitation of a response mediated by monocytes and Th1 cells" Biochimica et Biophysics Acta, vol. 1317, No. 3, 1996, pp. 183–191.

* cited by examiner

Structure of Matrix Extracellular Phosphoglycoprotein

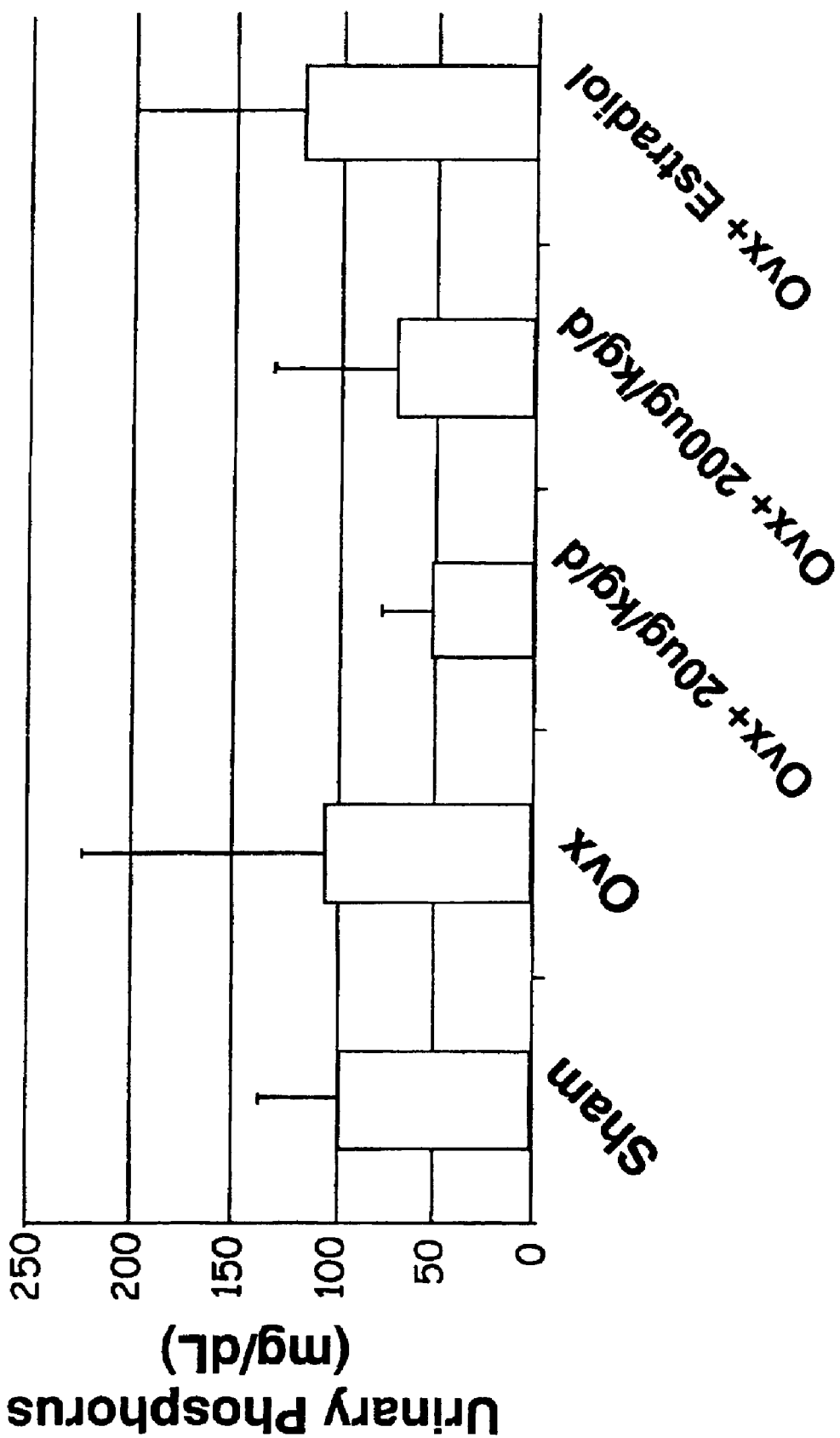

INTEGRIN BINDING MOTIF CONTAINING PEPTIDES AND METHODS OF TREATING SKELETAL DISEASES

CROSS-REFERENCE

This application is a continuation-in-part application of Ser. No. 09/641,034, filed Aug. 16, 2000, which is incorporated herein by reference in its entirety and to which application we claim priority under 35 USC § 120.

FIELD OF THE INVENTION

The invention relates generally to the field of peptides and more particularly to peptides and formulations thereof useful in treating skeletal diseases.

BACKGROUND OF THE INVENTION

It is well-documented that disorders of skeletal tissues and mineral metabolism cause numerous significant health problems on world-wide basis.

In humans, the maximum bone mass occurs between the age of 15 and 40 and is referred to as "peak bone mass." After such peak bone mass age, bone mass begins declining gradually and the mechanical strength of the bone is accordingly reduced. Consequently, when mechanical strength declines to a certain level, the individual is at greater risk of bone fracture. This natural occurrence is called osteoporosis if severe enough to be pathogenic.

The speed at which bone loss occurs differs among individuals, and especially with respect to gender. In females, the speed of bone loss accelerates immediately after menopause (See FIG. 1) because of a significant decline in available estrogen, a hormone which plays a critical role in maintaining healthy bone metabolism. Postmenopausal osteoporosis constitutes an important clinical problem because it afflicts significant numbers of women. Notably, the ratio of female to male osteoporosis patients is 3:1.

The majority of bone diseases are characterized by loss of bone minerals, weakening of bones and consequently, an increase of the frequency and severity of bone fractures, which are called "pathological fracture." In the elderly population, this has significant social ramifications as well, as many of those with bone fractures have difficulty with mobility, which often leads to the deterioration of other mental and physical functions, resulting in dementia, muscular weakness and/or fatigue. In addition, morbidity and pain are significantly increased by thrombotic events, such as pulmonary embolism which can occur as a result of hip or pelvic fractures.

In the United States alone, it is said that 52 million women over age of 45 will suffer from osteoporosis by 2000. Current worldwide osteoporosis population is around 200 million. Annual incidence of pathological fracture in the United States alone is approximately 1.5 million. It is estimated that annual medical costs for those osteoporosis patients in the United States and world are $14 billion and $60 billion, respectively.

Renal failure is also a significant health problem related to mineral metabolism and skeletal formation, and the number of its patients is increasing rapidly. Renal function is declining gradually over several to ten years period in these patients. When the renal function becomes approximately a quarter (¼) of the healthy level, the patients are classified to chronic renal failure. When it becomes approximately one sixth (⅙) thereof, they need to start dialysis and are called end stage renal disease (ESRD). In patients with chronic renal failure, serum levels of important minerals such as calcium and phosphate lose their normal homeostasis, which results in malformation of skeleton. It is called renal osteodystrophy (ROD), which is a secondary osteoporosis from renal failure. ROD can also cause pathological fracture like osteoporosis. The prevalence of end stage renal disease (ESRD) in the United States is rapidly increasing and about to reach 300 thousand in 2000. ROD affects most ESRD patients.

There are several other diseases of skeletal tissues and mineral metabolism such as Paget's Disease, rickets, osteopetrosis, hyperparathyroidism, and so forth and a number of patients are affected by these diseases.

Metabolically, bone is a highly active organ with bone resorption and formation occurring continuously (remodeling). Bone resorption is facilitated by osteoclasts which are differentiated from monocyte/macrophage lineage cells. Osteoclasts adhere to the surface of bone and degrade bone tissue by secreting acids and enzymes. Osteoblasts facilitate bone formation by adhering to degraded bone tissue and secreting bone matrix proteins, which are mineralized mostly by calcium and phosphate. Osteoblasts differentiate into bone cells (osteocytes), and become a part of bone tissue.

Numerous experimental approaches have been attempted to either accelerate bone formation or diminish bone resorption. For example, growth factors such as BMPs (bone morphogenetic proteins), TGFβ (transforming growth factor β), IGF (insulin-like growth factor), and fibroblast growth factor (FGF) are known to have potent biological activities in bone formation. In particular, a few subfamily molecules of BMP such as BMP-2 is regarded as one of the most potent growth factors for hard tissue. However, these factors have not been developed as therapeutic agents for systemic bone diseases. It is because none of them can be delivered to the bone selectively and some of these factors such as BMPs convert soft tissue into hard tissue. It is called ectopic calcification and is a critical adverse effect for them when they are used systemically. Further, the processes of bone formation and resorption are so closely connected and that makes selective increase of bone formation or selective inhibition of bone resorption extremely difficult.

Currently, there is a need for an effective treatment for bone loss. Therapeutic agents such as estrogen, calcitonin, vitamin D, fluoride, Ipriflavon, bisphosphonates, and a few others have failed to provide a satisfactory means of treatment. (Gennari et al., *Drug Saf.* (1994) 11(3):179–95).

Estrogen and its analogues are frequently administered to patients with postmenopausal osteoporosis. Estrogen replacement therapy involves administration of estrogen just prior to or after the onset of menopause. However, as is often the case with steroid hormones, the long term use of estrogen has significant adverse effects such as breast and other gynecological cancers (Schneider et al., *Int. J. Fertil. Menopausal Study* (1995) 40(1):40–53).

Calcitonin, an endogenous hormone produced by the thyroid, binds selectively to osteoclasts, via its receptor, and inactivates them. Since the osteoclast is the only cell which can dissolve bone tissue, calcitonin binding can block or slow down bone degradation caused by the osteoclast. However, this biological mechanism is very short-lived, as the osteoclasts become tolerant to this drug relatively quickly. Therefore, the use of calcitonin does not provide an effective therapeutic option.

Fluoride has been shown to increase bone mass when it is administered to humans. However, while bone mass is increased, mechanical strength is not. Therefore, despite the increase in apparent bone mass, the risk of fracture remains (Fratzl et al., *J. Bone Mineral Res.* (1994) 9(10) :1541–1549). In addition, fluoride administration has significant health risks.

Ipriflavon has been used to treat osteoporosis in limited areas in the world. However, the actual efficacy of this compound is questionable and it is not widely accepted as a useful therapeutic agent for bone diseases.

Bisphosphonates are compounds derivatized from pyrophosphate. Synthesis involves replacing an oxygen atom situated between two phosphorus atoms with carbon and modifying the carbon with various substituents. While bisphosphonates are known to suppress bone resorption, they have little effect on bone formation. Furthermore, bisphosphonates adhere to the bone surface and remain there for very long time causing a long-term decrease in bone tissue turnover. As bone tissue needs to be turned over continuously, this decrease in turnover ultimately results in bone deterioration (Lufkin et al., *Osteoporos. Int.* (1994) 4(6):320–322; Chapparel et al., *J. Bone Miner. Res.* (1995) 10(1):112–118).

Another significant problem with the agents described above is that with the exception of fluoride and ipriflavon, they are unsuitable for oral administration, and thus, must be given parenterally. Since bone disorders are often chronic and require long-term therapy, it is desirable that therapeutic agents be suitable for oral administration.

In summary, a significant need exists for a therapeutic agent which can prevent or treat bone loss. In particular, a new drug that can selectively increase bone formation and/or number of osteoblast without affecting bone resorption or soft tissue is highly desired.

Another major health problem relating to skeleton and mineral metabolism is that with teeth. In the United States alone, it is estimated that 67 million people are affected by periodontal disease and that the annual cost of its treatment is approximately $6.0 billion in 2000. It is said 90% of the entire population experience dental caries in their lives. The annual cost to treat them is over $50 billion per year in the United States alone.

Dental caries are a universal disease and affects children and adults. Periodontal disease, on the other hand, affects mostly adults, and in particular, the aged. In many cases, the patient's gum is inflamed and destroyed, and the alveolar bone that supports the teeth is deteriorated. Cement that composes the core of the root is also damaged, and subsequently, teeth fall out. One of the most common treatments for tooth loss involves the use of a dental implant. An artificial implant (osseointegrated dental implants) is placed in the space where the tooth was lost. In severe cases, an entire denture is replaced by implants. However, implants frequently loosen, or fall out because their fixation on the alveolar bone is not always successful. Since alveolar bone is somehow damaged in these patients, the implant cannot always be supported well by alveolar bone. When alveolar bone is severely damaged, autogenous bone grafting is performed. In this case, a bone graft taken from another skeletal tissue of the same patient is grafted in the damaged alveolar area so that the hard tissue is regenerated and sinus is elevated there. Since these treatments require expensive bio-compatible materials and/or highly skilled techniques, the cost of treatment is usually very high.

It is believed that dental caries are caused by acidic condition in the oral cavity. For instance, sugars are converted to acid and dissolve the surface of the teeth. Although only enamel and a part of dentin is affected in many cases, the damage can reach the pulp cavity in severe cases that cause significant pain. The most typical treatment is filling the caries lesion with non-degradable materials such as metals or metal oxide. Treatment of dental caries mostly depends upon those materials and the techniques by the dentists, which is often expensive.

Although a few therapeutic agents have been developed and used in dental area, they are generally only anti-inflammatory drugs, analgesics, and antibiotics. No generally effective therapeutic agent that directly improves periodontal hard tissues has been developed.

Another major clinical problem in mineral metabolism is excessive loss or waste of phosphate ($PO_4$) out of the body system. Phosphate plays variety of important roles in all living creatures. In vertebrates, phosphate is a major component of their skeleton. In all animals, phosphate is an essential component to build polynucleotide chains and cell membranes; phosphorylation and dephosphorylation of sugars and nucleotides are the most essential reactions in energy generation and consumption; and phosphorylation and dephosphorylation of proteins, sugars, and lipids are indispensable reactions for signal transduction in the cells. Therefore, a shortage of phosphate could even result in death.

In mammals, phosphate concentration in the body fluid is controlled within a range that allows all normal biological functions in the body. The kidney is the most important organ for controlling phosphate levels in the body. Glomeruli in the kidney filter phosphate constantly to the urine, and proximal tubules usually reabsorb approximately 80% of this filtered phosphate. If this reabsorbing function is damaged, excessive phosphate is lost into the urine, resulting in various clinical problems.

For instance, it is well known that the majority of kidney transplant patients experience excessive renal phosphate leakage, because the transplanted kidneys only marginally reabsorb the urinary phosphate to the circulation. The reasons for this poor reabsorbing activity on the part of transplanted kidneys are unknown. It frequently causes the patients malnutrition and secondary osteoporosis. This problem cannot be treated by a simple exogenous supplementation of phosphate. Similar renal phosphate leakage with unknown pathology is often observed in pediatric medicine, with outcomes such as malnutrition or growth retardation.

Health problems associated with circulating phosphate shortage is not limited to humans. Milking cows sometimes suffer from hypophosphatemia (too low phosphate in the blood) by overproduction of the milk. It not only deteriorates the nutritional quality of the milk but also often make the cows useless for milk production. It is as relatively common problem in dairy farms.

Clearly, there is a significant demand for a therapeutic agent that promotes regeneration of alveolar bone and/or teeth, increases the number and activity of odontoblasts/osteoblasts that help form dental tissues, and reduces renal phosphate secretion.

SUMMARY OF THE INVENTION

A class of compounds is disclosed which are useful in treating or preventing a condition associated with skeletal loss or weakness and/or which reduce renal phosphate excretion. The compounds are peptides or analogs thereof which comprise between 10 and 50 monomer (e.g. amino acids) units. The amino acid sequence comprises one or more of the following motifs: an integrin binding motif sequence; a glycosaminoglycan binding motif; and a calcium-binding motif. The amino acids may be in the D- or L-conformation. The remaining monomer units (the sequence other than the aforementioned motifs) in the compound may be amino acid analogs. Where the motif is an integrin binding motif, the remaining monomer units are preferably naturally occurring amino acids having a sequence which are substantially the same as an amino acid sequence contiguous with the RGD sequence in the naturally occurring protein, matrix extracellular phosphoglycoprotein (Rowe et. al., *Genomics* (2000) 67:56–68).

An aspect of the invention is a set of peptides and/or peptide analogs.

A feature of the invention is that a compound of the invention comprises one or more of the following motifs: an integrin binding motif sequence; a glycosaminoglycan-binding motif; and a calcium-binding motif. The amino acids may be in the D- or L-conformation.

An advantage of the invention is that a compound of the invention enhances skeletal growth.

Another advantage of the invention is that a compound of the invention enhances the number of osteoblast and possibly odontoblast cells on the surface of new skeletal or tooth growth.

Another advantage of the invention is that a compound of the invention reduces phosphate (Pi) loss from the body, as indicated by reduced urinary Pi leakage.

Another aspect of the invention is to provide a formulation for therapeutic use which comprises a sufficient concentration of a compound of the invention and can be administered to the pulp of teeth, the space between the root of teeth and gum, or alveolar bone to prevent the damage on teeth and/or alveolar bone or regenerate the hard tissue in the damaged teeth and/or alveolar bone.

Another aspect of the invention is to provide toothpaste which comprises a sufficient concentration of a compound of the invention to enhance tooth and/or alveolar bone growth on areas where deterioration has occurred, or to prevent such deterioration.

Yet another aspect of the invention is to provide a mouthwash which comprises a sufficient concentration of a compound of the invention to enhance tooth and/or alveolar bone growth on areas where deterioration has occurred, or to prevent such deterioration.

Still another aspect of the invention is a dental floss having coated thereon and/or embedded therein a compound of the invention in an amount such that repeated application to teeth and/or alveolar bone results in enhanced tooth and/or alveolar bone growth on areas where deterioration has occurred, or to prevent such deterioration.

A further aspect of the invention is a small adhesive patch for application on gum tissue of an individual, the patch comprising a therapeutically effective amount of a compound of the invention. The compound is slowly released from the patch into the gum, so that the released compound penetrates into the root of the teeth as well as the alveolar and/or jaw bones to prevent loss of such bones and/or to regenerate such bones.

An object of the invention is to provide a method of treating or preventing skeletal bone or dental bone loss by the administration/application of any formulation/composition of the invention.

These and other objects, advantages, and features of the invention will become apparent to those persons skilled in the art upon reading the details of the subject invention, as more fully described below.

BRIEF DESCRIPTIONS OF THE DRAWINGS

FIG. 1 is a graph showing the relationship between bone mass and age in humans.

FIG. 2 is a schematic drawing of a matrix extracellular phosphoglycoprotein wherein the area designated as "A" includes sequences which match peptides of the present invention and the area designated as "B" is a highly homologous motif to a group of bone-tooth matrix phosphoglycoproteins such as osteopontin (OPN), dentin sialophosphoprotein (DSPP), dentin matrix protein 1 (DMP1), and bone sialoprotein II (IBSP).

FIGS. 3A, 3B, 3C, and 3D are actual photographs of bone cross-sections (from a seven day mouse calvaria organ culture study) showing the effects of a control (FIG. 3A), fibroblast growth factor-1 (FGF-1) (FIG. 3B), and two peptides of the invention designated D-00004 and D-00006 (FIGS. 3C and 3D, respectively).

FIG. 6 is a graph showing the effect of D-00006 on urinary phosphate leakage.

DETAILED DESCRIPTION OF THE INVENTION

Figure 1:
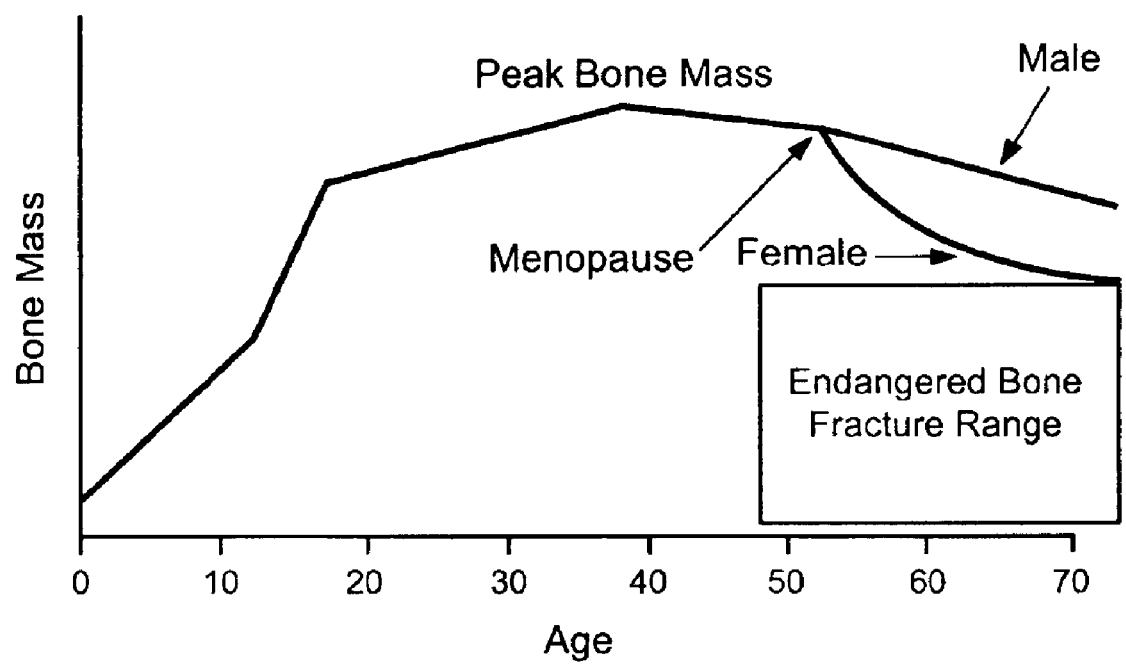
Figure 2:
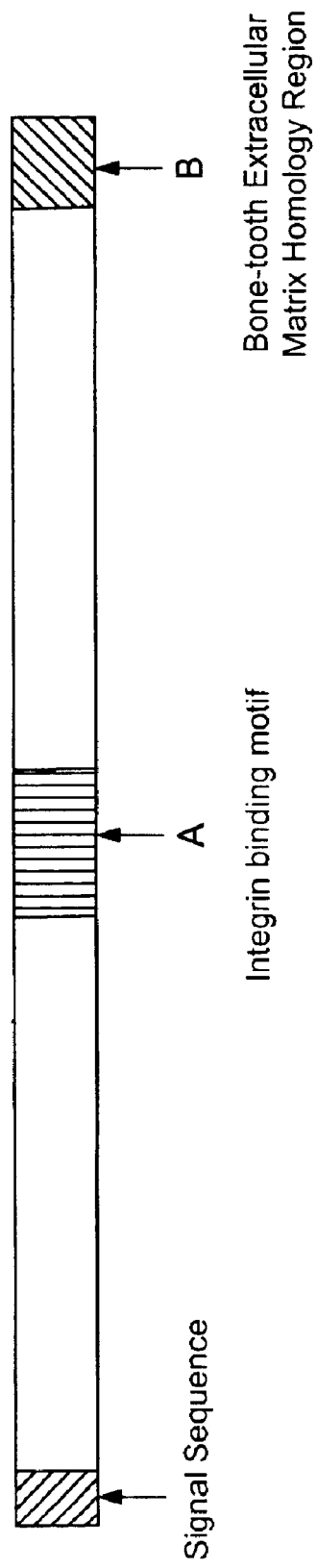

Before the peptides, analogs, formulations, and methodology of the present invention are described, it is to be understood that this invention is not limited to any particular embodiment described, as such may, of course, vary. It is also to be understood that the terminology used herein is with the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptide" includes a plurality of such peptides and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "peptide" and "peptidic compound" are used interchangeably herein to refer to a polymeric form of amino acids of from about 10 to about 50 amino acids, which can comprise coded and non-coded amino acids, chemically or biochemically modified or derivatized amino acids, L- or D-amino acids, peptides having modified peptide backbones, and peptides comprising amino acid analogs. The peptidic compounds may be polymers of: (a) naturally occurring amino acid residues; (b) non-naturally occurring amino acid residues, e.g. N-substituted glycines, amino acid substitutes, etc.; or (c) both naturally occurring and non-naturally occurring amino acid residues/substitutes. In other words, the subject peptidic compounds may be peptides or peptoids. Peptoid compounds and methods for their preparation are described in WO 91/19735, the disclosure of which is herein incorporated by reference.

The terms "treat", "treating", "treatment" and the like are used interchangeably herein and mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed the disease such as enhancing the effect of vitamin D. "Treating" as used herein covers treating a disease in a vertebrate and particularly a mammal and most particularly a human, and includes:

(a) preventing the disease from occurring in a subject which may be predisposed to the disease but has not yet been diagnosed as having it;

(b) inhibiting the disease, i.e. arresting its development; or (c) relieving the disease, i.e. causing regression of the disease.

The invention is particularly directed towards peptides which make it possible to treat patient's which have experienced bone loss or which would be expected to experience bone loss and thus is particularly directed towards preventing, inhibiting, or relieving the effects of bone loss. A subject is "treated" provided the subject experiences a therapeutically detectable and beneficial effect which may be measured based on a variety of different criteria including increased bone growth, increased bone strength or other characteristics generally understood by those skilled in the art to be desirable with respect to the treatment of diseases related to bone.

The term "antibody" is meant an immunoglobulin protein capable of binding an antigen. The term "antibody" as used herein is intended to include antibody fragments (e.g. F(ab')$_2$, Fab', and Fab) capable of binding an antigen or antigenic fragment of interest.

The term "binds specifically" is meant high avidity and/or high affinity binding of an antibody to a specific peptide—specifically a peptide of the invention. Antibody binding to its specific target epitope is stronger than the binding of the antibody to other epitopes on the peptide or to other epitopes on other peptides. Antibodies which bind specifically to a peptide of interest may be capable of binding to other peptides at a weak, yet detectable level (e.g. 10% or less of the binding shown to the peptide of interest). Such weak binding or background binding, is readily discernable from the specific antibody binding to the peptide of interest, e.g. by the use of appropriate controls.

The term "skeletal loss" refers to any situation in which skeletal mass, substance or matrix or any component of the skeleton, such as calcium and phosphate, is decreased or the bone is weakened such as in terms of its ability to resist being broken.

The term "skeleton" includes both bone and teeth. In the same manner, the term "skeletal" means both bone and teeth.

The term "osteoporosis" is intended to refer to any condition involving bone loss, i.e. involving a reduction in the amount of bone mass or substance resulting from any cause. The term particularly results in a bone loss resulting from demineralization of the bone, post menopausal or peri-menopausal estrogen decrease or nerve damage.

The terms "subject," "individual," "patient," and "host" are used interchangeably herein and refer to any vertebrate, particularly any mammal and most particularly including human subjects, farm animals, and mammalian pets.

Peptidic Compounds

A peptidic compound of the invention is a peptide comprising from 10 to 50 amino acids. The amino acids are preferably one of the twenty naturally occurring L-amino acids. However, D-amino acids may be present as may amino acid analogs. A peptide of the invention will comprise one or more of the following amino acid sequence motifs: an integrin binding motif such as RGD sequence; a glycosaminoglycan binding motif; and a calcium binding motif. Individual amino acids may be present in the peptides in either the L or the D isoform, but preferably in the L form. A peptide of the invention can be amidated or non-amidated on its C-terminus, or carboxylated or non-carboxylated on its N-terminus. The peptide of the invention may or may not contain a glycosaminoglycan binding motif such as SGDG (SEQ ID NO:41) sequence in L- or D-isomer form. A compound of the invention is still further characterized by biological activity i.e. it enhances skeletal growth as well as the growth or recruiting of osteoblast or odontoblast cells on surface of the new skeletal growth.

A peptidic compound of the invention exhibit one or more of the following properties when administered in an effective amount to an individual: (1) reduce bone loss; (2) increase bone mass; (3) increase bone strength; (4) reduce renal excretion of phosphate; and (5) reduce loss of phosphate from an individual.

Specific examples of peptides of the invention comprise seven to forty-seven amino acids on either side of the RGD sequence of the naturally occurring sequence of matrix extracellular phosphoglycoprotein. Thus, examples of peptides of the invention comprising sequences taken from the following sequence and including the RGD sequence shown in bold:

```
DSQAQKSPVKSKSTHRIQHNIDYLKHLSKVKKIPSDFEGSGYTDLQERGDNDISPFSGDG  (SEQ ID NO:1)
QPFKDIPGKGEATGPDLEGKDIQTGFAGPSEAESTHL
```

Specific examples of peptides of the invention which include the following: comprise the RGD sequence as the terminal sequence

```
AQKSPVKSKSTHRIQHNIDYLKHLSKVKKIPSDFEGSGYTDLQERGD           (SEQ ID NO:2)
RGDAQKSPVKSKSTHRIQHNIDYLKLHLSKVKKIPSDFEGSGYTDLQE          (SEQ ID NO:3)
DSQAQKSPVKSKSTHRIQHNIDYLKHLSKVKKIPSDFEGSGYTDRGD           (SEQ ID NO:4)
RGDSPVKSKSTHRIQHNIDYLKHLSKVKKIPSDFEGSGYTDLQE              (SEQ ID NO:5)
DSQAQKSPVKSKSTHRIQHNIDYLKHLSKVKKIPSDFEGSGRGD              (SEQ ID NO:6)
RGDTHRIQHNIDYLKHLSKVKKIPSDFEGSGYTDLQE                     (SEQ ID NO:7)
DSQAQKSPVKSKSTHRIQHNIDYLKHLSKVKKIPSDFERGD                 (SEQ ID NO:8)
RGDLKHLSKVKKIPSDFEGSGYTDLQE                               (SEQ ID NO:9)
DSQAQKSPVKSKSTHRIQHNIDYLKHLSKVKKIPSRGD                    (SEQ ID NO:10)
RGDLSKVKKIPSDFEGSGYTDLQE                                  (SEQ ID NO:11)
DSQAQKSPVKSKSTHRIQHNIDYLKHLSKRGD                          (SEQ ID NO:12)
RGDVKKIPSDFEGSGYTDLQE                                     (SEQ ID NO:13)
DSQAQKSPVKSKSTHRIQHNIDYLKRGD                              (SEQ ID NO:14)
RGDIPSDFEGSGYTDLQE                                        (SEQ ID NO:15)
DSQAQKSPVKSKSTHRIQHNIDRGD                                 (SEQ ID NO:16)
RGDDFEGSGYTDLQE                                           (SEQ ID NO:17)
DSQAQKSPVKSKSTHRRGD                                       (SEQ ID NO:18)
RGDGSGYTDLQE                                              (SEQ ID NO:19)
DSQAQKSPVKRGD                                             (SEQ ID NO:20)
RGDGYTDLQE                                                (SEQ ID NO:21)
DSQAQKSRGD                                                (SEQ ID NO:22)
RGDNDISPFSGDGQPFKDIPGKGEATGPDLEGKDIQTGFA                  (SEQ ID NO:23)
```

Specific examples of the peptides of the invention which comprise the RGD internally include the following:

```
NDI RGDSPFSGDGQPFKDIPGKGEATGPDLEGKDIQTGFA                 (SEQ ID NO:24)
NDISPF RGDSGDGQPFKDIPGKGEATGPDLEGKDI                      (SEQ ID NO:25)
NDISPFSGD RGDGQPFKDIPGKGEATGPDL                           (SEQ ID NO:26)
FSGDGQPFKDIPGKGEATGPDLEGKDIQTGFAGPSEAES RGDTHL            (SEQ ID NO:27)
IPGKGEATGPDLEGKDIQTGFAGPSE RGDAESTHL                      (SEQ ID NO:28)
EATGPDLEGKDIQTGFAG RGDPSEAESTHL                           (SEQ ID NO:29)
NDISPFSGDGQPFKD RGDIPGKGEATGPDLEGK                        (SEQ ID NO:30)
GKGEATGPDLEGKDI RGDQTGFAGPSEAESTHL                        (SEQ ID NO:31)
FSGDGQPFKDIPGKGEATG RGDPDLEGKDIQTGFAGPSEA                 (SEQ ID NO:32)
DGQPFKDIPGKGEATG RGDPDLEGKDIQTGF                          (SEQ ID NO:33)
```

-continued

| | |
|---|---|
| PFKDIPGKGEATG RGDPDLEGKDIQ | (SEQ ID NO:34) |
| DIPGKGEATG RGDPDLEGKDIQTGFAGP | (SEQ ID NO:35) |
| DGQPFKDIPGKGEATG RGDPDLEGKDIQTGF | (SEQ ID NO:36) |
| GKGEATG RGDPDLEGKDIQTGFAGPSEA | (SEQ ID NO:37) |
| EATG RGDPDLEGKDIQTGF | (SEQ ID NO:38) |
| EATG RGDPDLEGK | (SEQ ID NO:39) |
| EATG RGDPDL | (SEQ ID NO:40) |

In some embodiments, a peptide of the invention comprises a glycosaminoglycan-binding motif. A glycosaminoglycan binding motif has the consensus sequence SGXG (SEQ ID NO:50), wherein X is any amino acid. In some embodiments, a glycosaminoglycan binding motif has the sequence SGDG (SEQ ID NO:41).

In other embodiments, a peptide of the invention comprises a calcium binding motif. In some embodiments, a calcium binding motif has the sequence DNDISPFSGDGQ (SEQ ID NO:42). Also included in the term "calcium binding motif" are amino acid sequences that differ from SEQ ID NO:42 by one, two, three, four, five, six, seven, or eight amino acids. Of particular interest in many embodiments are motifs that conserve amino acids 1, 3, 5, 7, 9, and 12 of SEQ ID NO:42. Thus, in some embodiments, a peptide of the invention comprises, as a calcium-binding motif, the sequence DXDXSXFXGXXQ (SEQ ID NO:43), wherein X is any amino acid or amino acid analog.

In other embodiments, a calcium binding motif has the sequence $DX_1X_2X_3X_4X_5X_6X_7X_8X_9X_{10}X_{11}X_{12}$, wherein:
 $X_1$ is any amino acid;
 $X_2$ is D, N, or S;
 $X_3$ is I, L, V, F, Y, or W;
 $X_4$ is D, E, N, S, T, or G;
 $X_5$ is D, N, Q, G, H, R, or K;
 $X_6$ is G or P;
 $X_7$ is L, I, V, M, C;
 $X_8$ is D, E, N, Q, S, T, A, G, or C;
 each of $X_9$ and $X_{10}$ is independently any amino acid;
 $X_{11}$ is D or E; and
 $X_{12}$ is L, I, V, M, F, Y, or W.

In other embodiments, a calcium binding motif has the sequence $X_1X_2X_3X_4C(X_5)_nC(X_6)_mCX_7X_8X_9X_{10}X_{11}X_{12}X_{13}X_{14}C$, wherein
 each of $X_1$, $X_3$, and $X_4$ is independently D, E, Q, or N;
 each of $X_2$, $X_5$, $X_6$, $X_7$, $X_9$, $X_{10}$, $X_{11}$, $X_{12}$, and $X_{14}$ is independently any amino acid;
 n is 3–14;
 m is 3–7;
 $X_8$ is D or N; and
 $X_{13}$ is F or Y.

In other embodiments, a calcium binding motif has the sequence
$X_1X_2X_3X_4X_5DX_6X_7X_8X_9X_{10}X_{12}X_{13}X_{14}X_{15}X_{16}X_{17}X_{18}X_{19}X_{20}X_{21}$
wherein
 each of $X_1$ and $X_2$ is independently L, I, V, M, F, Y, or W;
 each of $X_3$, $X_4$, $X_6$, $X_7$, $X_8$, $X_{10}$, $X_{11}$, $X_{12}$, $X_{15}$, $X_{18}$, and $X_{19}$ is independently any amino acid;
 $X_5$ is L or K;
 $X_9$ is D or N;
 $X_{13}$ is D, N, S, or G;
 $X_{14}$ is F or Y;
 $X_{16}$ is E or S;
 $X_{17}$ is F, Y, V, or C;
 $X_{20}$ is L, I, V, M, F, or S;
 and $X_{21}$ is L, I, V, M, or F.

In other embodiments, a calcium binding motif has the sequence
$DX_1X_2X_3X_4X_5X_6GX_7DX_8X_9X_{10}GGX_{11}X_{12}X_{13}D$, wherein
 each of $X_1$, $X_3$, $X_4$, $X_5$, $X_6$, $X_7$, $X_8$, $X_{10}$, $X_{11}$, $X_{12}$, and $X_{13}$ is independently any amino acid; and
 each of $X_2$ and $X_9$ is independently L or I.

Calcium binding motifs are known in the art and have been described amply. See, for example, Springer et al. (2000) *Cell* 102:275–277; Kawasaki and Kretsinger (1995) *Protein Prof.* 2:305–490; Moncrief et al. (1990 *J. Mol. Evol.* 30-522–562; Chauvaux et al. (1990) *Biochem. J.* 265:261–265; Bairoch and Cox (1990) *FEBS Lett.* 269:454–456; Davis (1990) *New Biol.* 2:410–419; Schaefer et al. (1995) *Genomics* 25:638–643; and Economou et al. (1990) *EMBO J.* 9 :349–354. Any known calcium binding motif can be included in a peptidic compound of the invention.

A peptide of the invention may comprise one or more of an integrin binding motif, a glycosaminoglycan binding motif, and a calcium binding motif. The motifs may be present in the peptide in any order relative to one another. The motifs may be separated from one another by one, two, three, four, five, six, seven, eight, nine, or ten amino acids, or more. Furthermore, a motif may overlap with one or more other motifs. As one non-limiting example, a peptide having the sequence TDLQERGDNDISPFSGDGQPFKD (SEQ ID NO:49) comprises all three motifs, which overlap with one another.

All or any of the amino acids in the above sequences may be in the D- or L-conformation and may be substituted with equivalent analogs. The preferred embodiments comprise naturally occurring amino acids in the L-conformation.

All or any of the above sequences may be amidated, non-amidated, or otherwise modifed on their C-terminus, or carboxylated, non-carboxylated, or otherwise modified on their N-terminus.

In addition, multimers of any of the foregoing peptides are provided. Multimers include dimers, trimers, tetramers, pentamers, hexamers, etc. Thus, a peptide of the invention having a length of from about 10 to about 50 amino acids can be multimerized, optionally with an intervening linker, such that a subject peptide occurs in tandem arrays of two, three, four, five, six, or more copies. Furthermore, two or more different peptides of the invention can be multimerized with one another, forming "heteromultimers." Thus, e.g., a multimer may comprise a first and a second peptide, linked together by peptide bonds, optionally with a linker molecule such as one to ten glycine residues.

Peptidic compounds of the invention can be obtained using any known method, including, e.g., solid phase peptide synthesis techniques, where such techniques are known to those of skill in the art. Methods for synthesizing peptides are well known in the art and have been amply described in numerous publications, including, e.g., "The Practice of Peptide Synthesis" M. Bodanszky and A. Bodanszky, eds. (1994) Springer-Verlag; and Jones, The Chemical Synthesis of Peptides (Clarendon Press, Oxford) (1994). Generally, in such methods a peptide is produced through the sequential additional of activated monomeric units to a solid phase bound growing peptide chain. Also of interest is the use of submonomers in solid phase synthesis, as described in WO 94/06451, the disclosure of which is herein incorporated by reference.

Instead of solid phase synthesis, the subject peptidic compounds of the subject invention may be prepared through expression of an expression system comprising a polynucleotide encoding the peptidic compound. Any convenient methodology may be employed, where methodologies that may be employed typically include preparation of a nucleic acid molecule comprising a nucleotide sequence encoding the subject peptide, introduction of the encoding region into a vector for expression, transformation of a host cell with the vector, and expression and recovery of the product. Protocols for accomplishing each of the above steps are well known in art. See Sambrook, Fritsch & Maniatis, Molecular Cloning, A Laboratory Manual (Cold Spring Harbor Press, Inc.) (1989).

Matrix extracellular phosphoglycoprotein was cloned and characterized from a human tumor that caused osteomalacia in the patients. This extremely rare type of tumor called Oncogenic Hypophosphatemic Osteomalacia (OHO) tumor has been known to cause renal phosphate leak, hypophosphatemia (low serum phosphate levels), low serum calcitriol (1,25-vitamin D3), and abnormalities in skeletal mineralization (Osteomalacia). In the patients of OHO tumor, resection of the tumors results in remission of all of the above symptoms and it has been proposed that a circulating phosphaturic factor secreted from OHO tumor plays a role in osteomalacia. Matrix extracellular phosphoglycoprotein was proposed as a candidate of this phosphaturic factor (Rowe et. al., *Genomics* (2000) 67:56–68).

Phosphate plays a central role in many of the basic processes essential to the cell and the mineralization of skeleton. In particular, skeletal mineralization is dependent on the regulation of phosphate and calcium in the body and any disturbances in phosphate-calcium homeostasis can have severe repercussions on the integrity of bone.

In the kidney, phosphate is lost passively into the glomerular filtrate and is actively reabsorbed via a sodium (Na+) dependent phosphate cotransporter. In the intestine, phosphate is absorbed from foods. A sodium (Na+) dependent phosphate cotransporter was found to be expressed in the intestine and recently cloned (Hilfiker, PNAS 95(24) (1998), 14564–14569). The liver, skin and kidney are involved in the conversion of vitamin D3 to its active metabolite, calcitriol, which plays an active role in the maintenance of phosphate balance and skeletal mineralization.

Vitamin D deficiency causes rickets in children and osteomalacia in adults. Both conditions are characterized by failure of calcification of osteoid, which is the matrix of skeleton.

Thus, all of the humoral functions by matrix extracellular phosphoglycoprotein, namely, renal phosphate leak, hypophosphatemia (low serum phosphate levels), low serum calcitriol (1,25-vitamin D3), are harmful to healthy skeletal formation.

Matrix extracellular phosphoglycoprotein is a large polypeptide with 525 amino acid with short N-terminus signal sequence. Therefore, it is highly probable that this molecule is secreted from its producing cells into the body fluid and circulation. Out of its 525 amino acid sequence, a 23 amino acid motif on the C-terminus showed high similarities to a group of bone-tooth mineral matrix phosphoglycoproteins such as osteopontin (OPN), dentin sialophosphoprotein (DSPP), dentin matrix protein 1 (DMP1), and bone sialoprotein II (IBSP). It has been proposed that these bone-tooth mineral matrix phosphoproteins may play important roles in skeletal mineralization.

Notwithstanding the above observations about matrix extracellular phosphoglycoprotein, smaller peptide sequence containing integrin binding motif that is located within the amino acid sequence and far from its C-terminus sequence with a high degree of similarity to other bone-tooth mineral matrix phosphoglycoproteins demonstrated a very potent skeletal formation activity and increased the number of osteoblasts on such skeletal formation surface. The potency of such activities was equivalent to fibroblast growth factor (FGF). It was surprising in that small motifs located within a larger protein which has destructive functions on the skeleton demonstrated potent bone formation activity, and that such motifs were located far from the sequence which showed homology to other known bone-tooth matrix proteins.

Another surprising fact was that potent skeletal formation motifs of the invention contained an integrin binding motif, in particular, RGD sequence. It has been reported that a synthetic peptide containing the RGD sequence inhibited bone formation and resorption in a mineralizing organ culture system of fetal rat skeleton (Gronowicz et. al. Journal of Bone and Mineral Research 9(2):193–201 (1994)), that is a very similar experimental method used to test the subject of the present invention.

Further, the skeletal formation activity provided by the small peptides of the invention was as potent as that of an intact growth factor such as FGF.

Therapeutic Methods

The invention provides methods for reducing skeletal bone loss, methods for reducing renal phosphate leakage, methods for increasing bone mass, methods for increasing bone strength, and methods for reducing Pi excretion, comprising administering a peptidic compound of the invention. Typically, a peptidic compound of the invention is formulated with a pharmaceutically acceptable excipient for delivery to an individual in need thereof.

As used herein, an "effective amount" of a peptidic compound of the invention is an amount that reduces bone loss, and/or increases bone strength, and/or increases bone mass, and/or reduces phosphate loss, and/or reduces renal phosphate excretion by at least about 10%, at least about 15%, at least about 20%, at least about 25%, at least about 30%, at least about 35%, at least about 40%, at least about 45%, at least about 50%, at least about 55%, or at least about 60%, or more, when compared to a suitable control. Suitable controls are, in the case of experimental animals, an animal not treated with the peptide, e.g., treated with vehicle, or treated with an irrelevant peptide; and in the case of human subjects, a human subject treated with a placebo, or a human subject before treatment with a peptide of the invention.

In some embodiments, an effective amount of a peptidic compound of the invention is an amount that reduces renal phosphate excretion, and therefore reduces phosphate loss from an individual, by at least about 10%, at least about 15%, at least about 20%, at least about 25%, at least about 30%, at least about 35%, at least about 40%, at least about 45%, at least about 50%, at least about 55%, or at least about 60%, or more, when compared to a suitable control.

Whether a given peptide reduces bone loss, and/or increases bone strength, and/or increases bone mass, and/or reduces phosphate loss, and/or reduces renal phosphate excretion in an individual can be determined using any known assay to measure any known parameter associated with any one or more of reduced bone loss, increased bone strength, increased bone mass, reduces phosphate loss, and reduced renal phosphate excretion, including, but not limited to, serum and urinary phosphorus levels (e.g., using a colorimetric assay); serum and urinary calcium levels (e.g., using a colorimetric assay); serum and urinary creatinine levels; bone turnover marker levels (e.g., deoxypyrodinoline and osteocalcin); bone density (e.g., by in vivo bone densitometry); bone mechanical testing (e.g., lumbar vertebrae compression test; femoral shaft three point bending test; and the like); and the like. Such methods are standard in the art.

Individuals suitable for treatment with the methods of the invention are individuals having to believed to be at risk for, bone loss, or a disorder caused by bone loss, or a disorder whose sequelae include bone loss, including, but not limited to, dental caries, osteoporosis, Paget's disease, renal phosphate leakage, renal osteodystrophy, osteomalacia, osteodystrophy resulting from other causes, osteolysis mediated by cancer, fractures, and hyperparathyroidism. Such individuals include older individuals, post-menapausal women, kidney transplant recipients, and individuals having, or being at risk for, any of the aforementioned disorders.

Routes of Administration

Peptides of the invention are administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral and other parenteral routes of administration. Routes of administration may be combined, if desired, or adjusted depending upon the immunomodulatory nucleic acid molecule and/or the desired effect on the immune response. Peptides of the invention can be administered in a single dose or in multiple doses.

Peptides of the invention can be administered to a subject using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of peptides of the invention. Where systemic delivery is desired, administration typically involves invasive or systemically absorbed topical or mucosal administration of pharmaceutical preparations.

Peptides of the invention can also be delivered to the subject by enteral administration. Enteral routes of administration include, but are not necessarily limited to, oral and rectal (e.g., using a suppository) delivery.

Methods of administration of a peptide of the invention through the skin or mucosa include, but are not necessarily limited to, topical application of a suitable pharmaceutical preparation, transdermal transmission, injection and epidermal administration. Also contemplated for delivery of a peptide of the invention is a patch containing therein a peptide of the invention. A patch can be applied to the skin, or to other tissue, e.g., gum tissue. Any known patch delivery system that is suitable for oral delivery system can be used. See, e.g., U.S. Pat. No. 6,146,655.

Peptides of the invention can also be delivered to an individual by administering to the individual a nucleic acid molecule comprising a nucleotide sequence that encodes a peptide of the invention. The terms "polynucleotide" and "nucleic acid molecule" are used interchangeably herein to refer to polymeric forms of nucleotides of any length. The polynucleotides may contain deoxyribonucleotides, ribonucleotides, and/or their analogs. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons.

Expression vectors may be used to introduce a nucleic acid molecule encoding a subject peptide into a cell of an individual. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

An expression vector comprising a nucleotide sequence encoding a peptide of the invention may be introduced into tissues or host cells by any number of routes, including viral infection, microinjection, or fusion of vesicles. Jet injection may also be used for intramuscular administration, as described by Furth et al. (1992), *Anal Biochem*

205:365–368. The expression vector may be coated onto gold microparticles, and delivered intradermally by a particle bombardment device, or "gene gun" as described in the literature (see, for example, Tang et al. (1992), *Nature* 356:152–154), where gold microprojectiles are coated with the expression vector, then bombarded into skin cells.

Dosages

Although the dosage used will vary depending on the clinical goals to be achieved, a suitable dosage range is one which provides up to about 1 μg, to about 1,000 μg, to about 10,000 μg, to about 25,000 μg or about 50,000 μg of a peptide of the invention. Peptides of the invention can be administered in a single dosage or several smaller dosages over time. Alternatively, a target dosage of a peptide can be considered to be about 0.1–1000 μM, about 1–500 μM, or about 5–250 μM in a sample of host blood drawn within the first 24–48 hours after administration of the peptide.

The effect on bone loss, bone strength, phosphate excretion, or other parameter may be dose-dependent. Therefore, to increase potency by a magnitude of two, each single dose is doubled in concentration. Increased dosages may be needed to achieve the desired therapeutic goal. The invention thus contemplates administration of multiple doses to provide and maintain an effect on bone loss, bone strength, phosphate excretion, or other parameter. When multiple doses are administered, subsequent doses are administered within about 16 weeks, about 12 weeks, about 8 weeks, about 6 weeks, about 4 weeks, about 2 weeks, about 1 week, about 5 days, about 72 hours, about 48 hours, about 24 hours, about 12 hours, about 8 hours, about 4 hours, or about 2 hours or less of the previous dose.

In view of the teaching provided by this disclosure, those of ordinary skill in the clinical arts will be familiar with, or can readily ascertain, suitable parameters for administration of peptides according to the invention.

Formulations

In general, peptides are prepared in a pharmaceutically acceptable composition for delivery to a host. Pharmaceutically acceptable carriers preferred for use with the peptides of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a peptide of the invention may also be lyophilized using means well known in the art, for subsequent reconstitution and use according to the invention. Also of interest are formulations for liposomal delivery, and formulations comprising microencapsulated peptides.

In general, the pharmaceutical compositions can be prepared in various forms, such as granules, tablets, pills, suppositories, capsules, suspensions, salves, lotions and the like. In some embodiments, where delivery of a peptide of the invention is to oral tissues, a peptide of the invention may be formulated in a toothpaste, a mouthwash, or may be coated on or embedded in a dental floss. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, anti-pathogenic agents (e.g., antimicrobials, antibacterials, antivirals, antifungals, etc.), antioxidants, chelating agents, and inert gases and the like.

A peptidic compound of the invention can be administered with any other known agent that reduces bone loss. Thus, combination therapy is contemplated. Other agents that can be administered with a peptide of the invention include, but are not limited to, estrogen, calcitonin, vitamin D, fluoride, Ipriflavon, and bisphosphonate. A peptide of the invention can be administered simultaneously with (e.g., in admixture with, or in separate formulations) another agent that reduces bone loss; or can be administered within about 15 minutes, about 30 minutes, about 60 minutes, about 2 hours, about 5 hours, about 10 hours, about 12 hours, about 24 hours, about 36 hours, about 4 days, about 7 days, or more, of another agent that reduces bone loss. In addition, two or more peptides of the invention can be administered simultaneously or within about 15 minutes, about 30 minutes, about 60 minutes, about 2 hours, about 5 hours, about 10 hours, about 12 hours, about 24 hours, about 36 hours, about 4 days, about 7 days, or more of each other.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Synthesis of D-00001, etc.

Six different peptides were manually synthesized by the 9-fluorenylmethoxycarbonyl (Fmoc) strategy and prepared in the C-terminal amide form. The six peptides are as follows:

| | | |
|---|---|---|
| D-00001: | IPSDFEGSGYTDLQE | (SEQ ID NO:44) |
| D-00002: | DFEGSGYTDLQERGD | (SEQ ID NO:45) |
| D-00003: | YTDLQERGDNDISPF | (SEQ ID NO:46) |
| D-00004: | ERGDNDISPFSGDGQ | (SEQ ID NO:47) |
| D-00005: | NDISPFSGDGQPFKD | (SEQ ID NO:48) |
| D-00006: | TDLQERGDNDISPFSGDGQPFKD | (SEQ ID NO:49) |

(C-terminus amidated)

Amino acid derivatives and resins were purchased from Bachem, Inc., Torrance, Calif., and Novabiochem, La Jolla, Calif. The respective amino acids were condensed manually in a stepwise manner using 4-(2',4'-dimethoxyphenyl-Fmocaminomethyl)-phenoxy resin. N-methyl pyrrolidone was used during the synthesis as a solvent. For condensation, diisopropylcarbodiimide/N-hydroxybenzotriazole was employed, and for deprotection of $N^\alpha$-Fmoc groups, 20% piperidine in N-methyl pyrrolidone was employed. The following side chain protecting groups were used: Asn and Gln, trityl; Asp, Glu, Ser, and Thr, t-butyl; Arg, 2,2,5,7,8-pentamethylchroman-6-sulfonyl; and Lys, t-butoxycarbonyl. Resulting protected peptide resins were deprotected and cleaved from the resin using a trifluoroacetic acid-thioanisole-m-cresol-ethanedithiol-$H_2O$ (80:5:5:5:5, v/v) at 20° C. for 2 h. Resulting crude peptides were precipitated and washed with ethyl ether then purified by reverse-phase high performance liquid chromatography (using Vydac 5C18 column and a gradient of water/ acetonitrile containing 0.1% trifluoroacetic acid). All peptides were obtained with 5–20% yield (from the starting resin). Purity of the peptides was confirmed by analytical high performance liquid chromatography. Identity of the peptides was confirmed by a Sciex API IIIE triple quadrupole ion spray mass spectrometer.

Example 2

Fetal Mouse Calvarial Assay

Reagents

FGF-1 was purchased from Peprotech Inc. (Rocky Hill, N.J.). RGD-1, 2, 3, 4, 5 and 6 (referred to here as D-00001, D-00002, D-00003, D-00004, D-00005 and D-00006) were provided by Dr. Nomizu (Hokkaido University, Japan).

Mice

Pregnant ICR mice were purchased from SLC Japan Co. Ltd. (Shizuoka, Japan).

Mouse Calvarial Organ Culture

Mouse calvarial organ culture was performed as described in Mundy G et al. *Science* 286: 1946–1949, 1999 and Traianedes K et al. *Endocrinology* 139: 3178–3184, 1998. The calvaria from 4-days-old mice were excised and cut in half along the sagittal suture. Each half of the calvaria was placed on a stainless steel grid in a 12-well tissue culture dish (Asahi Glass Techno Corp., Funabashi, Japan). Each well contained 1.5 ml of BGj medium (Sigma, St. Louis, Mo.) supplemented with 0.1% bovine serum albumin (Sigma) and each compound. FGF-1 was used as a positive control as described by Mundy et al. The medium was changed at day 1 and 4, and the assay was terminated at day 7.

Histomorphometrical Analysis

Calvaria was fixed with 10% neutral-buffered formalin, decalcified with 4.13% EDTA and embedded in paraffin. 4 mm-thickness sections were made and stained with hematoxylin and eosin. New bone area was measured using Image-Pro Plus (Media Cybernetics, Silver Spring, Md.).

The six peptides of Example 1 were tested for their ability to enhance bone growth with the tests being carried out as described above in Example 2. The peptides which did not include the RGD sequence did not show positive results. The other four peptides showed positive results with the best results being obtained with the sequences

D-00004: ERGDNDISPFSGDGQ (SEQ ID NO:47), and

D-00006: TDLQERGDNDISPFSGDGQPFKD (SEQ ID NO:49).

Figure 3:
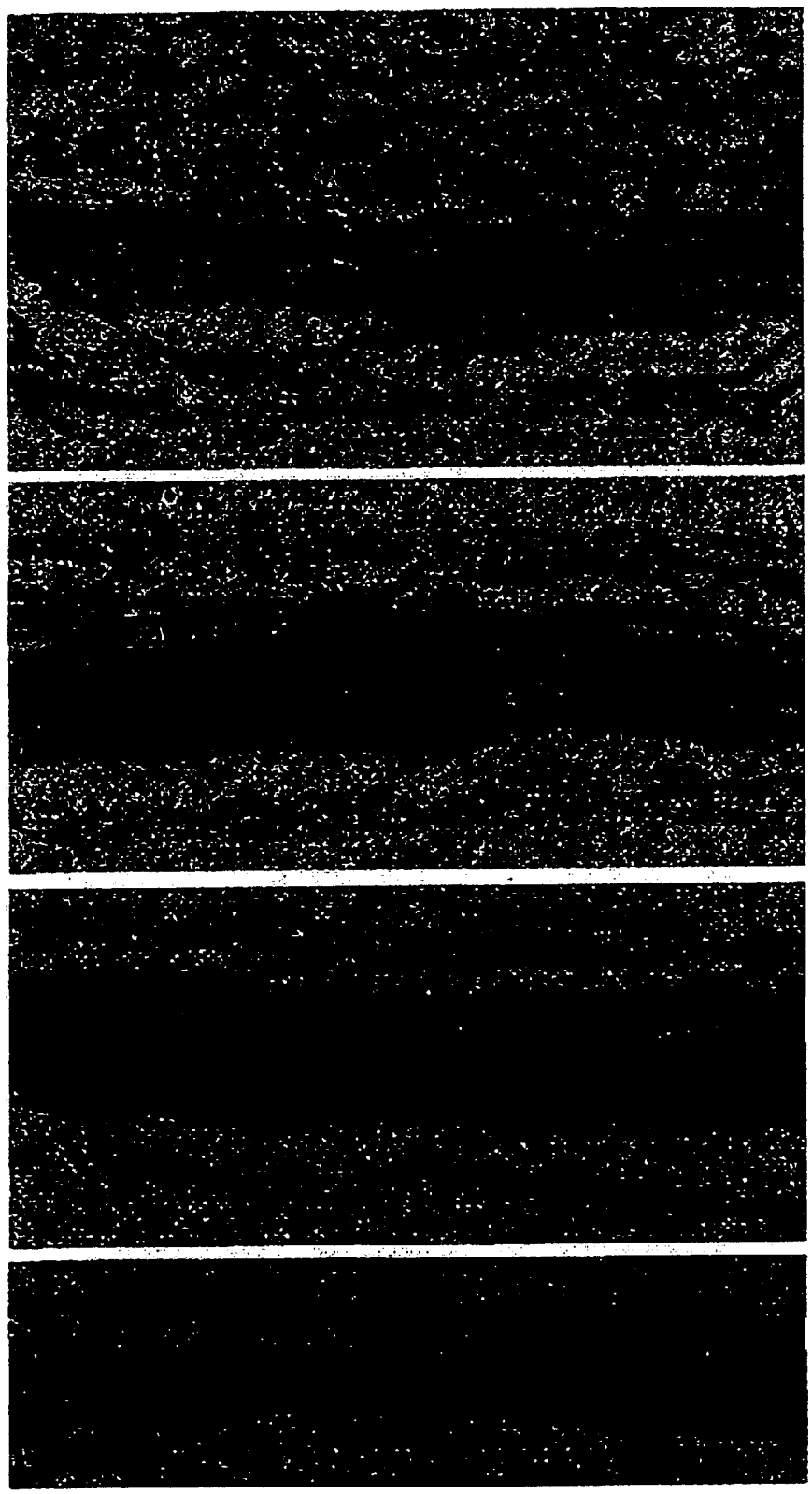
Figure 4:
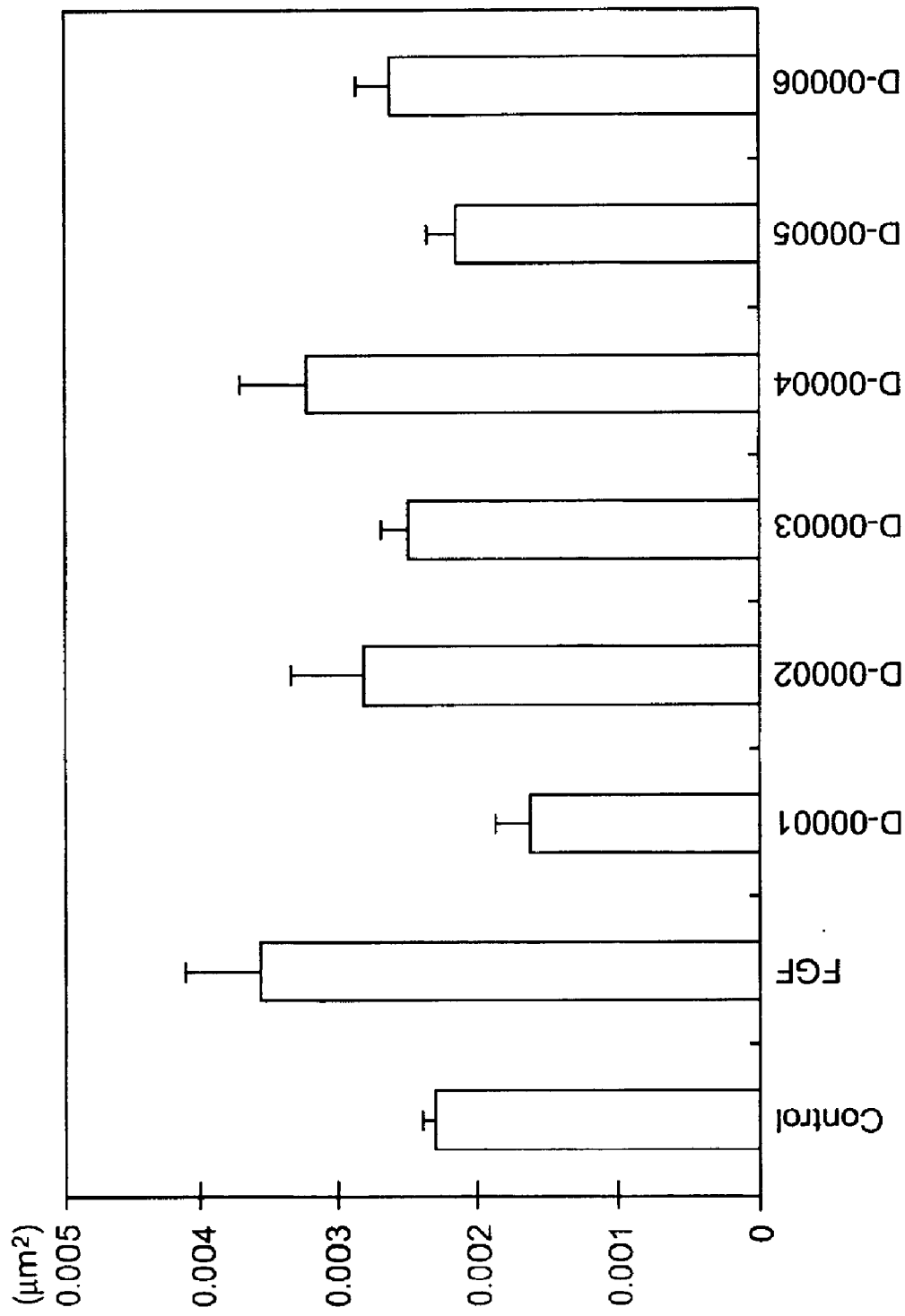
FIG. 4 is a graph comparing the effects of different compounds on calvaria.

The best results are in FIG. 3 (specifically FIG. 3C and 3D). Data from these results are graphically shown in FIGS. 4.

Example 3

In Vivo Bone Formation Study

Reagents

FGF-1 was purchased from Peprotech Inc. (Rocky Hill, N.J.). RGD-6 (referred to here as D-00006) was synthesized by CS Bio (San Carlos, Calif.) under the instruction of the inventors.

D-00006: TDLQERGDNDISPFSGDGQPFKD (SEQ ID NO:49).

Mice

Four week old mice were purchased from SLC Japan Co. Ltd. (Shizuoka, Japan) and randomized to three groups (n=5).

Mouse Calvaria Growth Assay

D-00006 (20 µg/kg/day), FGF-1 (12.5 µg/kg/day), or vehicle (saline) was subcutaneously injected into the soft tissues adjacent to the calvariae of the test animals. The daily amount of the samples were divided by two, respectively, and injected twice a day for five days. After 15 days of the last administration, the calvariae were excised and cut in half along the sagittal suture, and provided to the Histomorphometrical analysis.

Histomorphometrical Analysis

Calvaria was fixed with 10% neutral-buffered formalin, decalcified with 4.13% EDTA and embedded in paraffin. 4 mm-thickness sections were made and stained with hematoxylin and eosin. New bone area was measured using Image-Pro Plus (Media Cybernetics, Silver Spring, Md.).

Results

Figure 5:
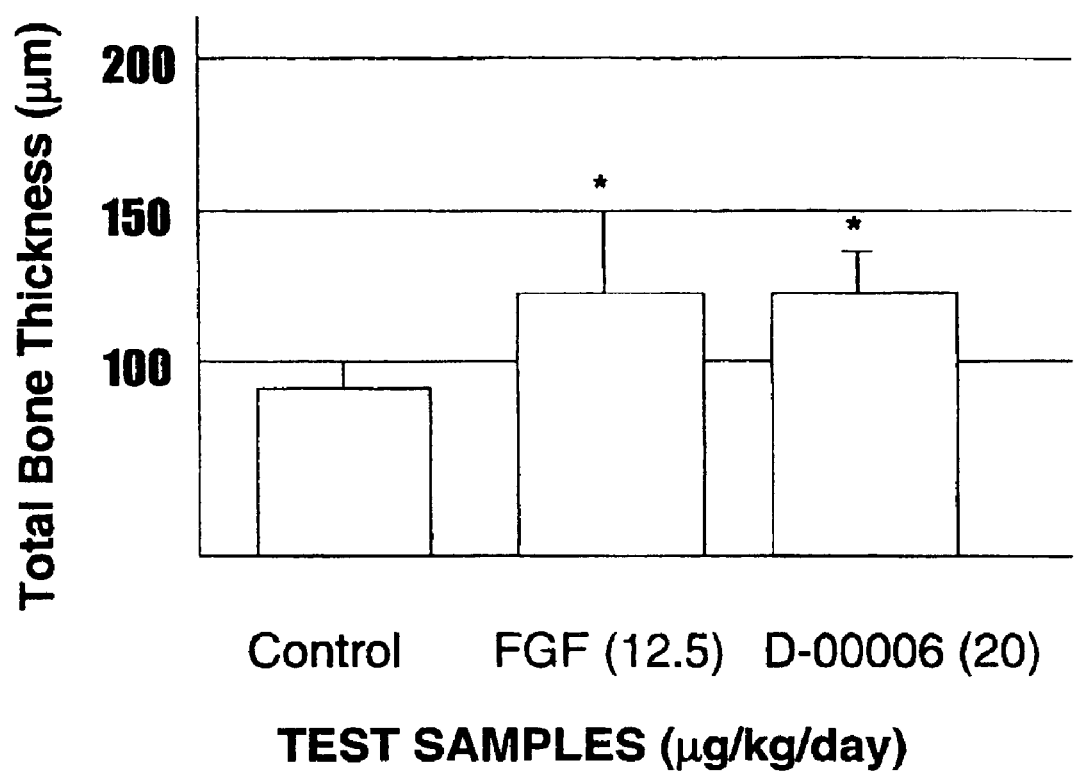
FIG. 5 is a graph showing the in vivo effects of D-00006.

The calvaria sections from the animals treated with FGF-1 showed a significant expansion of bone area as compared to the vehicle treated group. Those from the animals treated with D-00006 also demonstrated a significant expansion of bone area as compared to the vehicle treated group and the efficacy was equivalent to that of FGF-1. Data from these results are graphically shown in FIG. 5.

Example 4

Effect of D-00006 on Renal Phosphate Excretion

Experimental Design and Treatments

Forty 3-month old virgin female Sprague-Dawley rats (Harlan Sprague Dawley, Inc.) were acclimated for one week prior to beginning the experiments. Following the acclimatization period, the animal were randomized by initial body weight into treatment groups outlined in Table 1. Ovx: ovariectomized; LD: low dose; HD: high dose; Est: estradiol; D-00006 (TDLQERGDNDISPFSGDGQPFKD; SEQ ID NO:49).

TABLE 1

| Group No. | Description | Treatment | Dose-Level | # of Animals |
| --- | --- | --- | --- | --- |
| 1 | Sham | Vehicle | — | 8 |
| 2 | Ovx | Vehicle | — | 8 |
| 3 | Ovx + LD | D-00006 | 20 µg/kg/day | 8 |
| 4 | Ovx + HD | D-00006 | 200 µg/kg/day | 8 |
| 5 | Ovx + Est | 17 β-estradiol pellet implant and vehicle | 10 µg/kg/day | 8 |

One day prior to the initiation of treatments, the animals were anesthetized with a ketamin/xylazine anesthetic mixture, and animals in groups 2–5 were ovariectomized.

Urine was collected in metabolic cages on Day 41. Blood and urine samples were collected for chemistry and bone turnover markers assays at the end of the 41-day treatment period. Prior to urine and blood collections, the animals were placed in metabolic cages and deprived of food for an overnight fast period of 18 hours. Urine samples were collected and the volumes recorded. The urine samples were then centrifuges at approximately 3000×g for 10 minutes in a refrigerated centrifuge. The samples were filtered to remove contaminating sediments.

Serum and Urine Chemistry

Total serum calcium and creatinine levels were the same in all treatment groups, except that the Ovx animals treated with estradiol showed a slight increase in serum calcium. There was a dose-dependent increase in serum phosphorus in the D-0006 treated groups. Total urine volumes, collected over an 18-hour period, were the same in all groups. FIG. 6 shows the derived urine parameters.

The total amount of phosphorus in the 18-hour urine collections showed a significant decrease in D-00006 treated groups. As a result, D-00006 treated groups demonstrated lower phosphate clearance and a higher percentage of tubular reabsorption of phosphorus. D-00006 was clearly shown to be an agent that conserves phosphorus in the circulation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A toothpaste, comprising:
   a paste carrier, and
   [a therapeutically effective amount of] a peptide chosen from ERGDNDISPFSGDGQ (SEQ ID NO:47) and TDLQERGDNDISPFSGDGQPFKD (SEQ ID NO:49).

2. A mouthwash, comprising:
   an aqueous flavored solution; and
   [a therapeutically effective amount of] a peptide chosen from ERGDNDISPFSGDGQ (SEQ ID NO:47) and TDLQERGDNDISPFSGDGQPFKD (SEQ ID NO:49).

3. A patch for application on gum tissue of a patient; comprising: a patch carrier component; and
   [a therapeutically effective amount of] a peptide chosen from ERGDNDISPFSGDGQ (SEQ ID NO:47) and TDLQERGDNDISPFSGDGQPFKD (SEQ ID NO:49).

4. A dental floss comprising:
   a floss carrier component; and
   [a therapeutically effective amount of] a peptide chosen from ERGDNDISPFSGDGQ (SEQ ID NO:47) and TDLQERGDNDISPFSGDGQPFKD (SEQ ID NO:49).

* * * * *

UNITED STATES PATENT AND TRADEMARK OFFICE
CERTIFICATE OF CORRECTION

PATENT NO. : 6,911,425 B2
DATED : June 28, 2005
INVENTOR(S) : Kumagai, Yoshinari et al.

It is certified that error appears in the above-identified patent and that said Letters Patent is hereby corrected as shown below:

Column 41,
Lines 59 and 64, please delete "[a therapeutically effective amount of]";

Column 42,
Lines 58 and 62, please delete "[a therapeutically effective amount of]".

Signed and Sealed this

Thirteenth Day of September, 2005

JON W. DUDAS
*Director of the United States Patent and Trademark Office*

UNITED STATES PATENT AND TRADEMARK OFFICE
Certificate

Patented: June 28, 2005

Patent No. 6,911,425 B2

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Yoshinari Kumagai, Austin, TX (US); Toshiyuki Yoneda, San Antonio, TX (US); Russell Wayne Blacher, Castro Valley, CA (US); and Motoyoshi Nomizu, Tokyo (JP).

Signed and Sealed this Twenty-seventh Day of October 2009.

CECILIA TSANG
*Supervisory Patent Examiner*
Art Unit 1654

SEQUENCE LISTING

<160> NUMBER OF SEQ ID NOS: 50

<210> SEQ ID NO 1
<211> LENGTH: 97
<212> TYPE: PRT
<213> ORGANISM: Artificial Sequence
<220> FEATURE:
<223> OTHER INFORMATION: peptidic compound

<400> SEQUENCE: 1

Asp Ser Gln Ala Gln Lys Ser Pro Val Lys Ser Lys Ser Thr His Arg
1               5                   10                  15

Ile Gln His Asn Ile Asp Tyr Leu Lys His Leu Ser Lys Val Lys Lys
            20                  25                  30

Ile Pro Ser Asp Phe Glu Gly Ser Gly Tyr Thr Asp Leu Gln Glu Arg
        35                  40                  45

Gly Asp Asn Asp Ile Ser Pro Phe Ser Gly Asp Gly Gln Pro Phe Lys
    50                  55                  60

Asp Ile Pro Gly Lys Gly Glu Ala Thr Gly Pro Asp Leu Glu Gly Lys
65                  70                  75                  80

Asp Ile Gln Thr Gly Phe Ala Gly Pro Ser Glu Ala Glu Ser Thr His
                85                  90                  95

Leu

<210> SEQ ID NO 2
<211> LENGTH: 47
<212> TYPE: PRT
<213> ORGANISM: Artificial Sequence
<220> FEATURE:
<223> OTHER INFORMATION: peptidic compound

<400> SEQUENCE: 2

Ala Gln Lys Ser Pro Val Lys Ser Lys Ser Thr His Arg Ile Gln His
1               5                   10                  15

Asn Ile Asp Tyr Leu Lys His Leu Ser Lys Val Lys Lys Ile Pro Ser
            20                  25                  30

Asp Phe Glu Gly Ser Gly Tyr Thr Asp Leu Gln Glu Arg Gly Asp
        35                  40                  45

<210> SEQ ID NO 3
<211> LENGTH: 47
<212> TYPE: PRT

```
<213> ORGANISM: Artificial Sequence
<220> FEATURE:
<223> OTHER INFORMATION: peptidic compound

<400> SEQUENCE: 3

Arg Gly Asp Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
                20                  25                  30

Ile Pro Ser Asp Phe Glu Gly Ser Gly Tyr Thr Asp Leu Gln Glu
            35                  40                  45

<210> SEQ ID NO 4
<211> LENGTH: 47
<212> TYPE: PRT
<213> ORGANISM: Artificial Sequence
<220> FEATURE:
<223> OTHER INFORMATION: peptidic compound

<400> SEQUENCE: 4

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
                20                  25                  30

Ile Pro Ser Asp Phe Glu Gly Ser Gly Tyr Thr Asp Arg Gly Asp
            35                  40                  45

<210> SEQ ID NO 5
<211> LENGTH: 44
<212> TYPE: PRT
<213> ORGANISM: Artificial Sequence
<220> FEATURE:
<223> OTHER INFORMATION: peptidic compound

<400> SEQUENCE: 5

Arg Gly Asp Ser Pro Val Lys Ser Lys Ser Thr His Arg Ile Gln His
 1               5                  10                  15

Asn Ile Asp Tyr Leu Lys His Leu Ser Lys Val Lys Lys Ile Pro Ser
                20                  25                  30

Asp Phe Glu Gly Ser Gly Tyr Thr Asp Leu Gln Glu
            35                  40

<210> SEQ ID NO 6
<211> LENGTH: 44
<212> TYPE: PRT
<213> ORGANISM: Artificial Sequence
<220> FEATURE:
<223> OTHER INFORMATION: peptidic compound

<400> SEQUENCE: 6

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
                20                  25                  30

Ile Pro Ser Asp Phe Glu Gly Ser Gly Arg Gly Asp
            35                  40

<210> SEQ ID NO 7
<211> LENGTH: 37
<212> TYPE: PRT
<213> ORGANISM: Artificial Sequence
<220> FEATURE:
<223> OTHER INFORMATION: peptidic compound
```

```
<400> SEQUENCE: 7

Arg Gly Asp Thr His Arg Ile Gln His Asn Ile Asp Tyr Leu Lys His
 1               5                  10                  15

Leu Ser Lys Val Lys Lys Ile Pro Ser Asp Phe Glu Gly Ser Gly Tyr
             20                  25                  30

Thr Asp Leu Gln Glu
         35

<210> SEQ ID NO 8
<211> LENGTH: 41
<212> TYPE: PRT
<213> ORGANISM: Artificial Sequence
<220> FEATURE:
<223> OTHER INFORMATION: peptidic compound

<400> SEQUENCE: 8

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
             20                  25                  30

Ile Pro Ser Asp Phe Glu Arg Gly Asp
         35                  40

<210> SEQ ID NO 9
<211> LENGTH: 27
<212> TYPE: PRT
<213> ORGANISM: Artificial Sequence
<220> FEATURE:
<223> OTHER INFORMATION: peptidic compound

<400> SEQUENCE: 9

Arg Gly Asp Leu Lys His Leu Ser Lys Val Lys Lys Ile Pro Ser Asp
 1               5                  10                  15

Phe Glu Gly Ser Gly Tyr Thr Asp Leu Gln Glu
             20                  25

<210> SEQ ID NO 10
<211> LENGTH: 38
<212> TYPE: PRT
<213> ORGANISM: Artificial Sequence
<220> FEATURE:
<223> OTHER INFORMATION: peptidic compound

<400> SEQUENCE: 10

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
             20                  25                  30

Ile Pro Ser Arg Gly Asp
         35

<210> SEQ ID NO 11
<211> LENGTH: 24
<212> TYPE: PRT
<213> ORGANISM: Artificial Sequence
<220> FEATURE:
<223> OTHER INFORMATION: peptidic compound

<400> SEQUENCE: 11

Arg Gly Asp Leu Ser Lys Val Lys Lys Ile Pro Ser Asp Phe Glu Gly
 1               5                  10                  15
```

-continued

Ser Gly Tyr Thr Asp Leu Gln Glu
            20

<210> SEQ ID NO 12
<211> LENGTH: 32
<212> TYPE: PRT
<213> ORGANISM: Artificial Sequence
<220> FEATURE:
<223> OTHER INFORMATION: peptidic compound

<400> SEQUENCE: 12

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Arg Gly Asp
            20                  25                  30

<210> SEQ ID NO 13
<211> LENGTH: 21
<212> TYPE: PRT
<213> ORGANISM: Artificial Sequence
<220> FEATURE:
<223> OTHER INFORMATION: peptidic compound

<400> SEQUENCE: 13

Arg Gly Asp Val Lys Lys Ile Pro Ser Asp Phe Glu Gly Ser Gly Tyr
 1               5                  10                  15

Thr Asp Leu Gln Glu
            20

<210> SEQ ID NO 14
<211> LENGTH: 28
<212> TYPE: PRT
<213> ORGANISM: Artificial Sequence
<220> FEATURE:
<223> OTHER INFORMATION: peptidic compound

<400> SEQUENCE: 14

Asp Ser Gln Ala Gln Lys Ser Pro Val Lys Ser Lys Ser Thr His Arg
 1               5                  10                  15

Ile Gln His Asn Ile Asp Tyr Leu Lys Arg Gly Asp
            20                  25

<210> SEQ ID NO 15
<211> LENGTH: 18
<212> TYPE: PRT
<213> ORGANISM: Artificial Sequence
<220> FEATURE:
<223> OTHER INFORMATION: peptidic compound

<400> SEQUENCE: 15

Arg Gly Asp Ile Pro Ser Asp Phe Glu Gly Ser Gly Tyr Thr Asp Leu
 1               5                  10                  15

Gln Glu

<210> SEQ ID NO 16
<211> LENGTH: 25
<212> TYPE: PRT
<213> ORGANISM: Artificial Sequence
<220> FEATURE:
<223> OTHER INFORMATION: peptidic compound

<400> SEQUENCE: 16

Asp Ser Gln Ala Gln Lys Ser Pro Val Lys Ser Lys Ser Thr His Arg
 1               5                  10                  15

-continued

Ile Gln His Asn Ile Asp Arg Gly Asp
            20              25

<210> SEQ ID NO 17
<211> LENGTH: 15
<212> TYPE: PRT
<213> ORGANISM: Artificial Sequence
<220> FEATURE:
<223> OTHER INFORMATION: peptidic compound

<400> SEQUENCE: 17

Arg Gly Asp Asp Phe Glu Gly Ser Gly Tyr Thr Asp Leu Gln Glu
1               5                   10                  15

<210> SEQ ID NO 18
<211> LENGTH: 19
<212> TYPE: PRT
<213> ORGANISM: Artificial Sequence
<220> FEATURE:
<223> OTHER INFORMATION: peptidic compound

<400> SEQUENCE: 18

Asp Ser Gln Ala Gln Lys Ser Pro Val Lys Ser Lys Ser Thr His Arg
1               5                   10                  15

Arg Gly Asp

<210> SEQ ID NO 19
<211> LENGTH: 12
<212> TYPE: PRT
<213> ORGANISM: Artificial Sequence
<220> FEATURE:
<223> OTHER INFORMATION: peptidic compound

<400> SEQUENCE: 19

Arg Gly Asp Gly Ser Gly Tyr Thr Asp Leu Gln Glu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: peptidic compound

<400> SEQUENCE: 20

Asp Ser Gln Ala Gln Lys Ser Pro Val Lys Arg Gly Asp
1               5                   10

<210> SEQ ID NO 21
<211> LENGTH: 10
<212> TYPE: PRT
<213> ORGANISM: Artificial Sequence
<220> FEATURE:
<223> OTHER INFORMATION: peptidic compound

<400> SEQUENCE: 21

Arg Gly Asp Gly Tyr Thr Asp Leu Gln Glu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: peptidic compound

<400> SEQUENCE: 22

```
Asp Ser Gln Ala Gln Lys Ser Arg Gly Asp
1               5                  10
```

<210> SEQ ID NO 23
<211> LENGTH: 40
<212> TYPE: PRT
<213> ORGANISM: Artificial Sequence
<220> FEATURE:
<223> OTHER INFORMATION: peptidic compound

<400> SEQUENCE: 23

```
Arg Gly Asp Asn Asp Ile Ser Pro Phe Ser Gly Asp Gly Gln Pro Phe
1               5                  10                  15

Lys Asp Ile Pro Gly Lys Gly Glu Ala Thr Gly Pro Asp Leu Glu Gly
            20                  25                  30

Lys Asp Ile Gln Thr Gly Phe Ala
            35                  40
```

<210> SEQ ID NO 24
<211> LENGTH: 40
<212> TYPE: PRT
<213> ORGANISM: Artificial Sequence
<220> FEATURE:
<223> OTHER INFORMATION: peptidic compound

<400> SEQUENCE: 24

```
Asn Asp Ile Arg Gly Asp Ser Pro Phe Ser Gly Asp Gly Gln Pro Phe
1               5                  10                  15

Lys Asp Ile Pro Gly Lys Gly Glu Ala Thr Gly Pro Asp Leu Glu Gly
            20                  25                  30

Lys Asp Ile Gln Thr Gly Phe Ala
            35                  40
```

<210> SEQ ID NO 25
<211> LENGTH: 35
<212> TYPE: PRT
<213> ORGANISM: Artificial Sequence
<220> FEATURE:
<223> OTHER INFORMATION: peptidic compound

<400> SEQUENCE: 25

```
Asn Asp Ile Ser Pro Phe Arg Gly Asp Ser Gly Asp Gly Gln Pro Phe
1               5                  10                  15

Lys Asp Ile Pro Gly Lys Gly Glu Ala Thr Gly Pro Asp Leu Glu Gly
            20                  25                  30

Lys Asp Ile
        35
```

<210> SEQ ID NO 26
<211> LENGTH: 30
<212> TYPE: PRT
<213> ORGANISM: Artificial Sequence
<220> FEATURE:
<223> OTHER INFORMATION: peptidic compound

<400> SEQUENCE: 26

```
Asn Asp Ile Ser Pro Phe Ser Gly Asp Arg Gly Asp Gly Gln Pro Phe
1               5                  10                  15

Lys Asp Ile Pro Gly Lys Gly Glu Ala Thr Gly Pro Asp Leu
            20                  25                  30
```

<210> SEQ ID NO 27

```
<211> LENGTH: 45
<212> TYPE: PRT
<213> ORGANISM: Artificial Sequence
<220> FEATURE:
<223> OTHER INFORMATION: peptidic compound

<400> SEQUENCE: 27

Phe Ser Gly Asp Gly Gln Pro Phe Lys Asp Ile Pro Gly Lys Gly Glu
 1               5                  10                  15

Ala Thr Gly Pro Asp Leu Glu Gly Lys Asp Ile Gln Thr Gly Phe Ala
            20                  25                  30

Gly Pro Ser Glu Ala Glu Ser Arg Gly Asp Thr His Leu
        35                  40                  45

<210> SEQ ID NO 28
<211> LENGTH: 35
<212> TYPE: PRT
<213> ORGANISM: Artificial Sequence
<220> FEATURE:
<223> OTHER INFORMATION: peptidic compound

<400> SEQUENCE: 28

Ile Pro Gly Lys Gly Glu Ala Thr Gly Pro Asp Leu Glu Gly Lys Asp
 1               5                  10                  15

Ile Gln Thr Gly Phe Ala Gly Pro Ser Glu Arg Gly Asp Ala Glu Ser
            20                  25                  30

Thr His Leu
        35

<210> SEQ ID NO 29
<211> LENGTH: 30
<212> TYPE: PRT
<213> ORGANISM: Artificial Sequence
<220> FEATURE:
<223> OTHER INFORMATION: peptidic compound

<400> SEQUENCE: 29

Glu Ala Thr Gly Pro Asp Leu Glu Gly Lys Asp Ile Gln Thr Gly Phe
 1               5                  10                  15

Ala Gly Arg Gly Asp Pro Ser Glu Ala Glu Ser Thr His Leu
            20                  25                  30

<210> SEQ ID NO 30
<211> LENGTH: 33
<212> TYPE: PRT
<213> ORGANISM: Artificial Sequence
<220> FEATURE:
<223> OTHER INFORMATION: peptidic compound

<400> SEQUENCE: 30

Asn Asp Ile Ser Pro Phe Ser Gly Asp Gly Gln Pro Phe Lys Asp Arg
 1               5                  10                  15

Gly Asp Ile Pro Gly Lys Gly Glu Ala Thr Gly Pro Asp Leu Glu Gly
            20                  25                  30

Lys

<210> SEQ ID NO 31
<211> LENGTH: 33
<212> TYPE: PRT
<213> ORGANISM: Artificial Sequence
<220> FEATURE:
<223> OTHER INFORMATION: peptidic compound

<400> SEQUENCE: 31
```

```
Gly Lys Gly Glu Ala Thr Gly Pro Asp Leu Glu Gly Lys Asp Ile Arg
 1               5                  10                  15

Gly Asp Gln Thr Gly Phe Ala Gly Pro Ser Glu Ala Glu Ser Thr His
                20                  25                  30

Leu
```

<210> SEQ ID NO 32
<211> LENGTH: 40
<212> TYPE: PRT
<213> ORGANISM: Artificial Sequence
<220> FEATURE:
<223> OTHER INFORMATION: peptidic compound

<400> SEQUENCE: 32

```
Phe Ser Gly Asp Gly Gln Pro Phe Lys Asp Ile Pro Gly Lys Gly Glu
 1               5                  10                  15

Ala Thr Gly Arg Gly Asp Pro Asp Leu Glu Gly Lys Asp Ile Gln Thr
                20                  25                  30

Gly Phe Ala Gly Pro Ser Glu Ala
            35                  40
```

<210> SEQ ID NO 33
<211> LENGTH: 31
<212> TYPE: PRT
<213> ORGANISM: Artificial Sequence
<220> FEATURE:
<223> OTHER INFORMATION: peptidic compound

<400> SEQUENCE: 33

```
Asp Gly Gln Pro Phe Lys Asp Ile Pro Gly Lys Gly Glu Ala Thr Gly
 1               5                  10                  15

Arg Gly Asp Pro Asp Leu Glu Gly Lys Asp Ile Gln Thr Gly Phe
                20                  25                  30
```

<210> SEQ ID NO 34
<211> LENGTH: 25
<212> TYPE: PRT
<213> ORGANISM: Artificial Sequence
<220> FEATURE:
<223> OTHER INFORMATION: peptidic compound

<400> SEQUENCE: 34

```
Pro Phe Lys Asp Ile Pro Gly Lys Gly Glu Ala Thr Gly Arg Gly Asp
 1               5                  10                  15

Pro Asp Leu Glu Gly Lys Asp Ile Gln
                20                  25
```

<210> SEQ ID NO 35
<211> LENGTH: 28
<212> TYPE: PRT
<213> ORGANISM: Artificial Sequence
<220> FEATURE:
<223> OTHER INFORMATION: peptidic compound

<400> SEQUENCE: 35

```
Asp Ile Pro Gly Lys Gly Glu Ala Thr Gly Arg Gly Asp Pro Asp Leu
 1               5                  10                  15

Glu Gly Lys Asp Ile Gln Thr Gly Phe Ala Gly Pro
                20                  25
```

<210> SEQ ID NO 36
<211> LENGTH: 31

```
<212> TYPE: PRT
<213> ORGANISM: Artificial Sequence
<220> FEATURE:
<223> OTHER INFORMATION: peptidic compound

<400> SEQUENCE: 36

Asp Gly Gln Pro Phe Lys Asp Ile Pro Gly Lys Gly Glu Ala Thr Gly
 1               5                  10                  15
Arg Gly Asp Pro Asp Leu Glu Gly Lys Asp Ile Gln Thr Gly Phe
            20                  25                  30

<210> SEQ ID NO 37
<211> LENGTH: 28
<212> TYPE: PRT
<213> ORGANISM: Artificial Sequence
<220> FEATURE:
<223> OTHER INFORMATION: peptidic compound

<400> SEQUENCE: 37

Gly Lys Gly Glu Ala Thr Gly Arg Gly Asp Pro Asp Leu Glu Gly Lys
 1               5                  10                  15
Asp Ile Gln Thr Gly Phe Ala Gly Pro Ser Glu Ala
            20                  25

<210> SEQ ID NO 38
<211> LENGTH: 19
<212> TYPE: PRT
<213> ORGANISM: Artificial Sequence
<220> FEATURE:
<223> OTHER INFORMATION: peptidic compound

<400> SEQUENCE: 38

Glu Ala Thr Gly Arg Gly Asp Pro Asp Leu Glu Gly Lys Asp Ile Gln
 1               5                  10                  15
Thr Gly Phe

<210> SEQ ID NO 39
<211> LENGTH: 13
<212> TYPE: PRT
<213> ORGANISM: Artificial Sequence
<220> FEATURE:
<223> OTHER INFORMATION: peptidic compound

<400> SEQUENCE: 39

Glu Ala Thr Gly Arg Gly Asp Pro Asp Leu Glu Gly Lys
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: peptidic compound

<400> SEQUENCE: 40

Glu Ala Thr Gly Arg Gly Asp Pro Asp Leu
 1               5                  10

<210> SEQ ID NO 41
<211> LENGTH: 4
<212> TYPE: PRT
<213> ORGANISM: Artificial Sequence
<220> FEATURE:
<223> OTHER INFORMATION: glycosaminoglycan binding motif

<400> SEQUENCE: 41
```

Ser Gly Asp Gly
1

<210> SEQ ID NO 42
<211> LENGTH: 12
<212> TYPE: PRT
<213> ORGANISM: Artificial Sequence
<220> FEATURE:
<223> OTHER INFORMATION: calcium binding motif

<400> SEQUENCE: 42

Asp Asn Asp Ile Ser Pro Phe Ser Gly Asp Gly Gln
1               5                   10

<210> SEQ ID NO 43
<211> LENGTH: 12
<212> TYPE: PRT
<213> ORGANISM: Artificial Sequence
<220> FEATURE:
<223> OTHER INFORMATION: calcium-binding motif
<221> NAME/KEY: VARIANT
<222> LOCATION: 2, 4, 6, 8, 10, 11
<223> OTHER INFORMATION: Xaa = Any Amino Acid

<400> SEQUENCE: 43

Asp Xaa Asp Xaa Ser Xaa Phe Xaa Gly Xaa Xaa Gln
1               5                   10

<210> SEQ ID NO 44
<211> LENGTH: 15
<212> TYPE: PRT
<213> ORGANISM: Artificial Sequence
<220> FEATURE:
<223> OTHER INFORMATION: D-00001 peptide
<221> NAME/KEY: AMIDATION
<222> LOCATION: 15

<400> SEQUENCE: 44

Ile Pro Ser Asp Phe Glu Gly Ser Gly Tyr Thr Asp Leu Gln Glu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: D-00002 peptide
<221> NAME/KEY: AMIDATION
<222> LOCATION: 15

<400> SEQUENCE: 45

Asp Phe Glu Gly Ser Gly Tyr Thr Asp Leu Gln Glu Arg Gly Asp
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: D-00003 peptide
<221> NAME/KEY: AMIDATION
<222> LOCATION: 15

<400> SEQUENCE: 46

Tyr Thr Asp Leu Gln Glu Arg Gly Asp Asn Asp Ile Ser Pro Phe
1               5                   10                  15

```
-continued

<210> SEQ ID NO 47
<211> LENGTH: 15
<212> TYPE: PRT
<213> ORGANISM: Artificial Sequence
<220> FEATURE:
<223> OTHER INFORMATION: D-00004 peptide
<221> NAME/KEY: AMIDATION
<222> LOCATION: 15

<400> SEQUENCE: 47

Glu Arg Gly Asp Asn Asp Ile Ser Pro Phe Ser Gly Asp Gly Gln
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: D-00005 peptide
<221> NAME/KEY: AMIDATION
<222> LOCATION: 15

<400> SEQUENCE: 48

Asn Asp Ile Ser Pro Phe Ser Gly Asp Gly Gln Pro Phe Lys Asp
 1               5                  10                  15

<210> SEQ ID NO 49
<211> LENGTH: 23
<212> TYPE: PRT
<213> ORGANISM: Artificial Sequence
<220> FEATURE:
<223> OTHER INFORMATION: D-00006 peptide
<221> NAME/KEY: AMIDATION
<222> LOCATION: 15

<400> SEQUENCE: 49

Thr Asp Leu Gln Glu Arg Gly Asp Asn Asp Ile Ser Pro Phe Ser Gly
 1               5                  10                  15

Asp Gly Gln Pro Phe Lys Asp
            20

<210> SEQ ID NO 50
<211> LENGTH: 4
<212> TYPE: PRT
<213> ORGANISM: peptide
<220> FEATURE:
<223> OTHER INFORMATION: glycosaminoglycan binding motif
<221> NAME/KEY: VARIANT
<222> LOCATION: 3
<223> OTHER INFORMATION: Xaa = Any Amino Acid

<400> SEQUENCE: 50

Ser Gly Xaa Gly
 1
```